US005482635A

United States Patent [19]
Behan et al.

[11] Patent Number: 5,482,635
[45] Date of Patent: Jan. 9, 1996

[54] FABRIC CONDITIONER WITH DEODORANT PERFUME COMPOSITION

[75] Inventors: John M. Behan, Ashford; Christopher F. Clements, Folkestone; John R. Martin, Birkenhead; Keith D. Perring, Ashford, all of United Kingdom

[73] Assignee: Lever Brothers Company, New York, N.Y.

[21] Appl. No.: 443,254

[22] Filed: May 17, 1995

Related U.S. Application Data

[63] Continuation of Ser. No. 235,600, Apr. 29, 1994, abandoned, which is a continuation-in-part of Ser. No. 89,154, Jul. 8, 1993, abandoned, which is a division of Ser. No. 697,918, May 1, 1991, abandoned, which is a continuation-in-part of Ser. No. 539,636, Jun. 18, 1990, abandoned.

[30] Foreign Application Priority Data

Jun. 19, 1989 [GB] United Kingdom ............... 8914055
Apr. 30, 1993 [GB] United Kingdom ............... 9308953

[51] Int. Cl.$^6$ ............................................. D06M 13/35
[52] U.S. Cl. ................... 252/8.6; 252/8.8; 512/1; 512/11; 512/10; 512/20; 512/27
[58] Field of Search ............... 252/8.8, 8.6; 512/1, 512/11, 10, 20, 27

[56] References Cited

U.S. PATENT DOCUMENTS

| | | | |
|---|---|---|---|
| 4,134,838 | 1/1979 | Hooper et al. | 252/8.8 |
| 4,278,658 | 7/1981 | Hooper et al. | 424/65 |
| 4,337,180 | 6/1982 | Kiwala | 252/522 R |
| 4,352,748 | 10/1982 | Traas et al. | 252/522 R |
| 4,650,603 | 3/1987 | Sprecker | 252/522 R |
| 4,698,180 | 10/1987 | Pavlin | 252/522 R |
| 4,840,792 | 6/1989 | Joulain et al. | 424/76.1 |
| 4,915,866 | 4/1990 | Mookherjee | 252/95 |
| 4,929,599 | 5/1990 | Giersch et al. | 512/18 |

FOREIGN PATENT DOCUMENTS

| | | |
|---|---|---|
| 3172 | 7/1979 | European Pat. Off. . |
| 3171 | 7/1979 | European Pat. Off. . |
| 5618 | 11/1979 | European Pat. Off. . |
| 147191 | 7/1985 | European Pat. Off. . |
| 299561 | 1/1989 | European Pat. Off. . |
| 545556 | 6/1993 | European Pat. Off. . |
| 1530436 | 4/1966 | France . |
| 247946 | 12/1987 | France . |
| 1472536 | 5/1977 | United Kingdom . |

OTHER PUBLICATIONS

Kling et al., *Woodworth & Schlosberg's Experimental Psychology*; pp. 73–79, no month 1971.
Hoffmann, "Malodor Control–A Review"; *Perfumer & Flavorist*, vol. 11, Jun./Jul. 1986, pp. 2–8.
Seventh Detergent Congress in Barcelona, Spain in Mar. 1976, VII Jornadas del Comite Espanol de la Detergenica on pp. 201–228 and English translation included.

*Primary Examiner*—C. Melissa Bonner
*Attorney, Agent, or Firm*—A. Kate Huffman

[57] ABSTRACT

A fabric conditioning product which may be used during the rinsing or tumble drying of fabrics after washing, contains a perfume composition which contains specified ketones and salicylates. The perfumes inhibit development of human body malodour on the fabrics when worn and the combination of specified materials makes it possible to avoid inclusion of individual components with powerful, unacceptable odors.

12 Claims, No Drawings

FABRIC CONDITIONER WITH DEODORANT PERFUME COMPOSITION

RELATED APPLICATIONS

This is a continuation application of Ser. No. 08/235,600, filed Apr. 29, 1994, now abandoned, which is a continuation-in-part of U.S. Ser. No. 08/089,154, filed Jul. 8, 1993, now abandoned which is a divisional of Ser. No. 07/697,918, filed May 1, 1991, now abandoned which in turn is a continuation-in-part of Ser. No. 07/539,636 filed Jun. 18, 1990, now abandoned.

FIELD OF THE INVENTION

This invention relates to perfume compositions, that is to say compositions of fragrance materials and to fabric conditioning compositions containing such perfume compositions to give a deodorant effect.

SUMMARY OF THE PRIOR ART

European Patent 3172 and U.S. Pat. Nos. 4304679, 4322308, 4278658, 4134838, 4288341, 4289641 and 4663068 all describe perfume compositions which exhibit a deodorant action, (i.e. inhibit development of human body malodour). U.S. Pat. No. 4134838 teaches that such perfume compositions may be included in a fabric conditioning product used to soften fabrics during rinsing or drying.

A difficulty with the perfume compositions disclosed in these documents is that they include components which frequently give them strong, powerful odors which are difficult for the perfumer to blend out and which can limit the usefulness of the compositions when used to perfume some other product such as a detergent composition, fabric conditioner or personal care product. This has created a necessity for compromise between deodorant efficacy and acceptability as a fragrance.

SUMMARY OF THE PRESENT INVENTION

It has surprisingly been found that certain compositions of fragrance materials can confer deodorant effects in use even though they have in themselves a low or imperceptible level of fragrance (low odor intensity). This is of advantage in many applications where an intense fragrance is not desired, while a deodorant effect is to be welcomed.

Other, related, compositions can provide deodorant effects in use while possessing a widely acceptable fragrance.

Broadly, the present invention provides a perfume composition in which at least 30% by weight of the composition is constituted by materials from the categories of materials set out below:

at least 7%, preferably at least 10% and generally not more than 50% by weight of the perfume composition of one or more aromatic methyl ketones of general formula

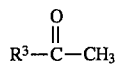

which $R^3$ is an aromatic group such that the molecular weight of the ketone is from 170 to 300; and at least 3% and generally not more than 60% by weight of the perfume composition of one or more salicylates of general formula

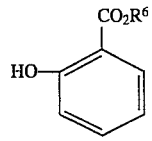

in which $R^6$ is an aliphatic group, optionally containing not more than one olefinic double bond, and optionally bearing an aromatic substituent group, such that the molecular weight of the salicylate is in the range 190 to 230;

all the percentages being by weight of the whole perfume composition.

If such perfumes are to have a fragrance, they preferably include at least 5% and generally not more than 70% by weight of the perfume composition of one or more ingredients selected from alcohols of general formula:

acetates of general formula

and propionates of general formula

in which $R^4$ is an aliphatic group, optionally containing not more than one olefinic double bond, and optionally bearing an aromatic substituent group, such that the molecular weight of an alcohol $R^4OH$ is in the range 130 to 180 and $R^5$ is an aliphatic group optionally containing not more than one olefinic double bond, and optionally bearing an aromatic substituent group, such that the molecular weight of an acetate or propionate ester is in the range 180 to 210.

It is preferred that the perfume compositions with a perceptible fragrance contain at least 4% of one or more of the above alcohols of formula $R^4OH$ and at least 5% of one or more of the above esters of formula $CH_3CO_2R^5$ or $C_2H_5CO_2R^5$.

In contrast to the teaching of abovementioned application 07/973,364, the perfume compositions of the present invention do not require ethers as essential ingredients.

Perfume compositions of this invention may optionally include at least 0.05% of one or more ethers of the general formula

in which the groups $R^1$ and $R^2$ are connected only through the ether oxygen atom, and are aliphatic or aromatic groups such that the ether has a molecular weight of 150 to 200.

In one aspect this invention provides a fabric conditioning product for use in the treatment of fabrics, during rinsing or drying which composition contains a fabric softening agent together with a perfume composition as set forth above.

In another aspect this invention provides a method of softening fabrics by use of such a composition.

DETAILED DESCRIPTION

The categories of perfume materials referred to above will now be reviewed in turn.

Aromatic methyl ketones

The group $R^3$ in the formula

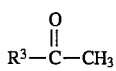

given above can contain up to approximately 18 carbon atoms and will usually contain at least 9. Examples of suitable ketones are:

or beta methyl naphthyl ketone;

Musk ketone, which is a trivial name for 4-tert-butyl-3,5-dinitro-2,6-dimethyl acetophenone;

1,1,2,4,4,7-Hexamethyl-6-acetyl-1,2,3,4-tetrahydronaphthalene, available under the trademark "TONALID" from Polak's Frutal Works;

5-Acetyl-1,1,2,3,3,6-hexamethylindane, available under the trademark "PHANTOLIDE" from Polak's Frutal Works;

4-Acetyl-6-tert-butyl-1,1-dimethylindane, available under the trademark "CELESTOLIDE" from International Flavours & Fragrances;

6-Acetyl-1-isopropyl-2,3,3,5-tetramethylindane, available under the trademark "TRASEOLIDE" from Quest International;

1,1,4,4-Tetramethyl-6-acetyl-7-ethyl-1,2,3,4-tetrahydronaphthalene, available under the trademark "VERSALIDE" from Polak's Frutal Works.

The amount of each ketone, if more than one is present, will desirably be at least 1% or at least 2% by weight of the perfume composition. The total amount of these ketones may extend up to 35% or even beyond up to 50% by weight of the perfume composition. Possibly, however, the amount does not exceed 24%, 20% or 18% by weight of the perfume composition and may lie in a range from 7 to 15%.

Salicylates

In the formula

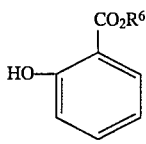

given above, the group $R^6$, like the groups $R^4$ and $R^5$ mentioned above, is aliphatic, possibly with an aromatic substituent, and either without olefinic unsaturation, or with one double bond at most. The requirement as to molecular weight permits groups $R^6$ of up to 7 carbon atoms. Examples of suitable salicylates are:

Amyl salicylate
Benzyl salicylate
Butyl salicylate
cis-3-hexenyl salicylate
Cyclohexyl salicylate
Hexyl salicylate
Isoamyl salicylate
Isobutyl salicylate.

Salicylates can be used in large amounts, such as up to 50 or 60% by weight of the composition. At least 5%, may be preferred, and especially 5% to 20% or 30% by weight.

It may be preferred that the total amount of the said ketones and salicylates is not more than 35% by weight of the perfume composition.

Alcohols

The group $R^4$ in the formula $R^4OH$ given above is aliphatic but may have an aromatic substituent. Olefinic unsaturation may be present to the extent of one double bond, but may be entirely absent. Aliphatic groups are therefore alkyl, alkenyl, cycloalkyl and cycloalkenyl, optionally bearing an aromatic substituent group.

The stated molecular weight range of 130 to 180 permits up to 11 carbon atoms in the group $R^4$. Usually there will be at least 8. Examples of suitable alcohols are:

Cinnamic alcohol
Citronellol
Decanol
Dihydromyrcenol
Dimethylheptanol
Dimethyloctanol
Dimethyl benzyl carbinol
Isononanol
Isoborneol
4-isopropyl cyclohexanol
4-isopropyl cyclohexyl methanol
Isopulegol
Menthol
Myrtenol
Nonanol
Octanol
para-menthan-7-ol
2-tert-butylcyclohexanol
4-tert-butylcyclohexanol
3-methyl-5-phenyl pentanol, available under the trademark "PHENOXANOL"
2-Phenylpropanol
3-Phenylpropanol
9-Decen-1-ol, available under the trademark "ROSALVA"
alpha-Terpineol
beta-Terpineol
Tetrahydrogeraniol
Tetrahydrolinalol
3,5,5-Trimethylcyclohexanol
Undecanol
10-Undecen-1-ol.

The amount of individual alcohols is preferably at least 1% or at least 2% by weight of the perfume composition. The total amount of alcohol is preferably at least 4%, more preferably at least 5% but will generally not exceed 50% by weight of the perfume composition. From 7% to 30%, especially 7% to 20%, is preferred.

Esters

These esters are acetates and propionates. Like the group $R^4$, discussed above, the group $R^5$ in the formula $CH_3CO_2R^5$ and $C_2H_5CO_2R^5$ given above is aliphatic, possibly with an aromatic substituent, and with no more than one olefinic double bond, if any.

The molecular weight range permits propionates in which $R^5$ has up to 9 carbon atoms, and acetates in which $R^5$ has up to 10 carbon atoms.

Examples of suitable esters are:

3a,4,5,6,7,7a-hexahydro-4,7-methano-1(3)H-inden-6-yl propanoate, available under the trademark "FLOROCYCLENE"; 3-acetoxymethyl-4,7,7-trimethylbicyclo [4.1.0]-hept-2-ene, available under the trademark "FORESTONE";

3a,4,5,6,7,7a-hexahydro-4,7-methano-1(3)H-inden-6-yl acetate, available under the trademark "JASMACYCLENE";

Bornyl acetate
Cinnamyl propionate
Citronellyl acetate
Decyl acetate
Dihydroterpinyl acetate
Dimethyl benzyl carbinyl acetate
3,5,5-trimethylhexyl acetate, available as "Inonyl acetate"
Isobornyl acetate
Isopulegol acetate
Menthyl acetate
Myrtenyl acetate
Myrtenyl propionate
Nonyl acetate
Terpinyl acetate
Terpinyl propionate
2-tert-butylcyclohexyl acetate
4-tert-butylcyclohexyl acetate
Tetrahydrogeranyl acetate
Tetrahydrolinalyl acetate
10-Undecenyl acetate.

The amounts of individual esters preferably are at least 1% or at least 2%. The total amount of esters can range up to as much as 40% by weight of the perfume composition or more. 5% to 30% is preferred. The amount may possibly be at least 10% by weight.

Ethers

These ethers are non-cyclic, in the sense that the ether oxygen atom is not part of a ring, although the groups $R^1$ and $R^2$ in the formula $R^1OR^2$ given above may themselves incorporate rings. Each of these groups may be aliphatic or aromatic e.g. alkyl, cycloalkyl, alkenyl, cycloalkenyl, phenyl, naphthyl, aryl substituted aliphatic or alkyl substituted aromatic. Preferably neither group contains more than one olefinic double bond.

The molecular weight range approximately corresponds to ethers containing up to about 13 or 14 carbon atoms in all. There will usually be at least 9 carbon atoms, depending however on any side chains present.

Examples of ethers in this category are:

Phenylethyl isoamyl ether, available under the trademark "ANTHER";

Phenylethyl n-butyl ether;

Benzyl isoamyl ether;

Dihydroanethole, which is 4-propylanisole, more properly known as methyl 4-propylphenyl ether;

Diphenyl oxide;

p-tert butylphenyl methyl ether, available under the trademark "EQUINOL";

Ethyl naphthyl ether, also known under the trademark "NEROLIN";

Methyl naphthyl ether, available under the trademark "YARA".

The last five of the above ethers have at least one aromatic group which is phenyl, naphthyl or substituted phenyl or naphthyl.

Many of these ethers are effective when used in rather small amounts. Generally if more than one ether is present, each ether will be present in an amount of at least 0.1% by weight of the perfume composition. It will generally be desirable that the total amount of these ethers does not exceed 20% by weight of the perfume composition and possibly does not exceed 10% if a mixed aliphatic aromatic ether is present. A quantity of not over 6% is preferred, for methyl naphthyl ether and/or ethyl naphthyl ether. The total of all ethers in this category may well not exceed 6%.

A material may have a structure such that it can be placed in more than one of the above categories. If so, the material should be placed in only a single category.

Preferably, however, the assignment of materials to categories is carried out in such a way that any material which is simultaneously more than one of ether, ester, alcohol or ketone is first classified as an ester, alcohol, ketone or ether in that order of priority and then either attributed to the appropriate category if the material satisfies the requirements for that category, or else excluded from all categories.

The effect of this preferred approach is that the category of alcohols shall not then include any material which is an ester (regardless of whether it is an acetate, propionate or some other ester). The category of ketones shall not include any material which is an ester or contains a hydroxyl group. The category of ethers shall not include any material which is an ester, or contains a hydroxyl or keto group.

For example on this basis a material which was both an ether and an alcohol would be treated as an alcohol and if it satisfied the above definition of category alcohols $R^4OH$, or else excluded entirely. Similarly an ester which was not of formula:

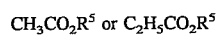

$$CH_3CO_2R^5 \text{ or } C_2H_5CO_2R^5$$

would not be placed in any category.

As a practical matter, available salicylates do not have other functionality. However, it should be the case that the categories of ethers, ketones, acetates and propionates do not include any material which is a saticylate.

Further materials

The perfume compositions of this invention may include other materials in addition to those in the above categories. These may include at least 2% by weight of the perfume composition falling within a sixth category of specified materials which are not all structurally related. Members of this further category are:

1) Aldehydes of formula $R^7CHO$ having molecular weight 180–220 in which $R^7$ is aliphatic or aryl-aliphatic, like $R^4$ and $R^5$. Especially envisaged are hexyl cinnamic aldehyde, and 2-methyl-3(para-t-butylphenyl)propionaldehyde which is available under the trademark "LILIAL".

2) 1,3,4,6,7,8-hexahydro-4,6,6,7,8,8-hexamethylcyclopenta-2-benzopyran, available under the trademark "GALAXOLIDE" from International Flvaours & Fragrances.

It may be the case that the categories if ethers, alcohols, acetates and propionates do not include any material which contains an aldehyde group.

Some compositions exemplified in prior documents have included natural essential oils. Many such oils contain substantial amounts of terpenes and terpene aldehydes. These natural oils tend to give strong odors and preferably are not used in amounts greater than 25%, better not greater than 10% by weight of the composition.

Perfume compositions of this invention which have a low odor may be defined as having a less intense odor than a 10% by weight solution of benzyl acetate in dipropylene glycol. Assessment of odor intensity is desirably carried out by a panel of assessors who have been trained to assess the intensity of perfume samples.

The perfume compositions are particularly intended to be incorporated in fabric conditioning products used during rinsing or drying of fabrics, notably to enhance softness of fabrics.

Fabric conditioning products are used during the rinsing and/or drying of fabrics to confer a benefit to the fabrics and to the user's perception of the fabrics.

The main benefits delivered by such products are softness, fragrance and anti-static. This invention is particularly concerned with products which provide softness. The perfume of this invention will then provide fragrance.

A fabric softening product contains at least one softening agent which functions to give the fabric a softer handle. Frequently such agents also provide an anti-static benefit. Usually such agents are cationic, nonionic, amphoteric or zwitterionic materials, Many fabric softening products take the form of compositions intended to be added to rinse water. The fabric softening agents are then materials with low solubility in water, and which deposit on the fabrics. Typically the solubility in acidified water at 20° C. is less than 10 g/liter, preferably less than 1 g/liter. When added to rinse water such materials form a dispersed phase which is then able to deposit on fabrics which are being rinsed in the water.

An alternative type of fabric softening product is an article such as an impregnated sheet or a porous sachet which is placed in a tumble dryer. The fabric softening agent is arranged to melt at the temperature in the dryer. It then transfers from the article to the fabrics in the dryer.

For such products the fabric softening agents may be similar to those used in a composition which is added to rinse water.

Many commercial important fabric softening agents are organic compounds containing quaternary nitrogen and at least one carbon chain of 6 to 30 carbon atoms, e.g. in an alkyl, alkenyl or aryl substituted alkyl or alkenyl group with at least six aliphatic carbon atoms.

Other fabric softening agents are the corresponding tertiary amines and imidazolines, other aliphatic alcohols, esters, amines or carboxylic acids incorporating a C8 to C30 alkyl, alkenyl or acyl group, including esters of sorbitan and esters of polyhydric alcohols, mineral oils, polyols such as polyethylene glycol, and also clays. Some of these materials may be used jointly with others rather than alone. Another class of materials used as an adjunct to a fabric softening agent is hydrophobically modified cellulose ethers.

Some specific instances of fabric softening agents are:
1) Acyclic quaternary ammonium compounds of the formula (I)

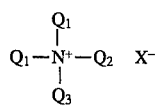

Wherein each $Q_1$ is a hydrocarbyl group containing from 15 to 22 carbon atoms. $Q_2$ is a saturated alkyl or hydroxy alkyl group containing from 1 to 4 carbon atoms. $Q_3$ may be as defined for $Q_1$ or $Q_2$ or may be phenyl and $X^-$ is an anion preferably selected from halide, methyl sulphate and ethyl sulphate radicals.

Throughout this discussion of fabric softening agents the expression hydrocarbyl group refers to alkyl or alkenyl groups optionally substituted or interrupted by functional groups such as —OH, —O—, CONH, —COO—, etc.

Representative examples of these quaternary softeners include ditallow dimethyl ammonium chloride; ditallow dimethyl ammonium methyl sulphate; dihexadecyl dimethyl ammonium chloride; di(hydrogenated tallow) dimethyl ammonium methyl sulphate or chloride; di(coconut)dimethyl ammonium chloride dihexadecy diethyl ammonium chloride; dibehenyl dimethyl ammonium chloride.

Ditallow dimethyl ammonium chloride, di(hydrogenated tallow)dimethyl ammonium chloride, di(coconut)dimethyl ammonium chloride and di(coconut)dimethyl ammonium methosulphate are preferred.

Examples of commercially available materials in this class are ARQUAD 2C, ARQUAD 2HT, ARQUAD 2T (all Ex Akzo Chemie), PRAPAGEN WK, PRAPAGEN WKT, DODIGEN 1828 (all Hoechst). QUERTON 4BG, QUERTON 442 (all Keno Gard), AMMONYX KP, AMMONYX SKD (all Mill Master-Onyx), SYNPROLAM FS (ICI).

2) Alkoxylated Polyamines

Alkoxylated polyamines of general formula (II) have been disclosed in EP 406 A1 (Procter)

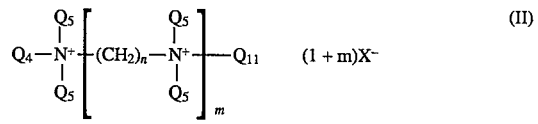

Each $Q_4$ is a hydrocarbyl group containing from 10 to 30 carbon atoms. The $Q_5$ groups may be the same or different each representing hydrogen, $(-C_2H_4O)_pH$, $(C_3H_6O)_qH$, $(C_2H_4O)_p$, $(C_3H_6O)_q,H$, an alkyl group containing from 1 to 3 carbon atoms or the group $(CH_2)_{n'}N(Q_5)_2$; n and n' are each an integer from 2 to 6, m is an integer from 1 to 5 and p, q and (p'+q') may be numbers such that (p+q+p'+q') does not exceed 25. $X^-$ is an anion.

Alkoxylated polyamines suitable for use herein include N-tallowyl, NN'N'-tris(2 hydroxyethyl)-1,3-propane diamine di-hydro chloride; N-cocyl N,N,N',N' pentamethyl-1,3 propane diammonium dichloride or dimethosulphate; N-stearyl N,N',N' tris(2-hydroxyethyl) N,N1'dimethyl-1,3 propanediammonium dimethyl sulphate; N-palmityl N,N', N'tris(3-hydroxypropyl)-1,3-propanediammonium dihydrobromide; N-tallowyl N-(3 -aminopropyl)-1,3-propanediamine trihydrochloride.

3. Diamido Quaternary Ammonium Salts

Diamido quaternary salts of general formula (III) are also known to be useful as fabric softening agents.

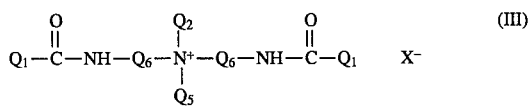

(III)

$Q_6$ is a divalent alkylene group containing from 1 to 3 carbon atoms. $Q_1$, $Q_2$, $Q_5$ and $X^-$ are as defined previously.

Examples of suitable materials are methylbis (tallowamidoethyl)(2-hydroxyethyl)ammonium methyl sulphate and methyl bis(hydrogenated tallowamido ethyl)(2 hydroxyethyl)ammonium methyl sulphate. These materials are available from Sherex Chem Co under trade names VARISOFT 222 and VARISOFT 110 respectively and under the trade name ACCOSOFT from Stepan.

4. Ester Quaternary Ammonium Salts

A number of ester group containing quaternary ammonium salts, including those disclosed in EP 345842 A2 (Procter), EP 239910 (Procter) and US 4137180 (Lever) and incorporated herein by reference, are known to be particularly useful as softening materials. These materials can be represented by generic formulae (IV) and (V) below.

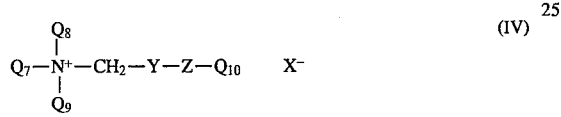

(IV)

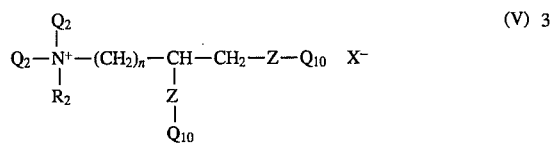

(V)

In formula (IV) $Q_7$ is a hydrocarbyl group containing 1 to 4 carbon atoms, $Q_8$ is $(CH_2)_n$—Z—$Q_{10}$ where n is an integer from 1 to 4 or —$Q_{10}$. $Q_9$ is an alkyl or hydroxyalkyl group of 1 to 4 carbon atoms, or is as defined for $Q_8$. $Q_{10}$ is a hydrocarbyl group containing from 12 to 22 carbon atoms and Y can be —CH(OH)—$CH_2$— or $Q_6$, as previously defined. Z can be —O—C(O)—O, —C(O)—O or —O—C(O)— and $X^-$ is an anion.

In formula (V) the symbols $Q_2$, $Q_{10}$, Z and $X^-$ have the meanings defined previously.

Examples of suitable materials based on formula IV are N,N-di(tallowyl-oxyethyl)-N,N-dimethyl ammonium chloride; N,N-di(2-tallotloxy-2-oxo-ethyl)-N,N-dimethyl ammonium chloride; N,N-di(2-tallowyloxyethylcarbonyl oxyethyl)-N,N-dimethyl ammonium chloride; N-(2 -tallowloxy-2-ethyl)-N-(2-tallowyl oxo-2-oxyethyl)-N,N-dimethyl ammonium chloride; N,N,N-tri(tallowyl-oxyethyl)-N-methyl ammonium chloride; N-(2-tallowyloxy-2 -oxyethyl)-N-(tallowyl-N,N-dimethyl)-ammonium chloride. Tallowyl may be replaced with cocoyl, palmoyl, lauryl, oleyl, stearyl and palmityl groups. An illustrative example of a formula V material is 1,2-ditallowyloxy-3-trimethyl ammoniopropane chloride.

Examples of commercially available materials can be obtained under the trade name STEPANTEX VRH 90 (Stepan), AKYPOQUAT (Chem-Y) and as mixtures of mono and ditallow esters of 2,3-dihydroxy propane trimethyl ammonium chloride (HOECHST).

5. Quaternary Imidazolinium Salts

A further class of cationic softener materials is the imidazolinium salts of generic formula (VI).

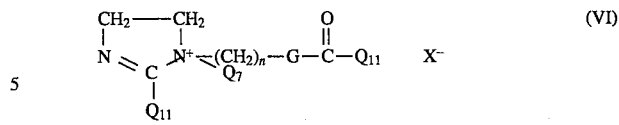

(VI)

Wherein $Q_{11}$ is a hydrocarbyl group containing from 6 to 24 carbon atoms, G is —N(H)—, or —O—, or $NQ_2$, n is an integer between 1 and 4, and $Q_7$ is as defined above.

Preferred imidazolinium salts include 1-methyl-1 -(tallowylamido)ethyl-2tallowyl-4,5 dihydro imidazolinium methosulphate and 1-methyl-1-(palmitoylamido)ethyl-2 -octadecyl-4,5-dihydroimidazolinium chloride. Other useful imidazolinium materials are 2-heptadecyl-1-methyl-1-(2 stearylamido)ethyl imidazolinium chloride and 2 -lauryl-1-hydroxyethyl-1-oleyl imidazolinium chloride. Also suitable are the imidazolinium fabric softening components of US 4127489 incorporated here by reference. Representative commercially available materials are VARISOFT 475 (Sherex) and REWOQUAT W7500 (Rewo).

6. Primary Secondary and Tertiary Amines

Primary, secondary and tertiary amines of general formula (VII) are useful as softening agents.

(VII)

Wherein $Q_{11}$ is a hydrocarbyl group containing from 6 to 24 carbon atoms, $Q_{12}$ is hydrogen or a hydrocarbyl group containing from 1 to 22 carbon atoms and $Q_{13}$ can be hydrogen or $Q_7$. Preferably amines are protonated with hydrochloric acid, orthophosphoric acid or citric acid or any other similar acids for use in fabric conditioning compositions of this invention.

7. Alkoxylated Amines

Alkoxylated amines of general formula (VIII) are also useful as components of this invention.

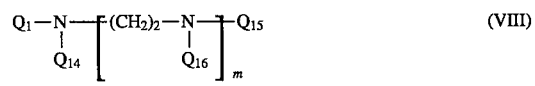

(VIII)

Wherein $Q_{14}$ is $(C_2H_4O)_xH$, $Q_{15}$ is $(C_2H_4O)_yh$ and $Q_{16}$ is $(C_2H_4O)_zH$ and x+y is within the range 2 to 15 and x+y+z is within the range 3 to 15, m can be 0, 1 or 2 and $Q_1$ is as previously defined.

Examples of these materials are monotallow-dipolyethoxyamine containing from 2 to 30 ethylene oxide units, tallow N,N',N' tris(2-hydroxyethyl)-1,3 propylene diamine or $C_{10}$ to $C_{18}$ alkyl-N-bis(2-hydroxyethyl)amines. Examples of commercially available materials are available under the trade names ETHOMEEN and ETHODUOMEEN (Akzo).

8. Cyclic Amines

Other useful materials are dialkyl cyclic amines represented by formula (IX).

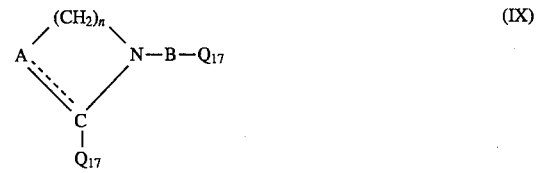

(IX)

Wherein the groups $Q_{17}$ are independently selected from hydrocarbyl groups containing from 8 to 30 carbon atoms and A can be oxygen (—O—) or nitrogen (—N=) preferably nitrogen; B is selected from $Q_6$ as defined earlier or the group —$Q_{18}$—T—C(O)— where $Q_{18}$ is either $Q_6$ or (—$C_2H_4O$—)$_m$ with m being an integer from 1 to 8 and T being selected from oxygen or $NQ_{13}$.

Illustrative materials are 12-stearyl oxyethyl-2-stearyl imidazoline, 1-stearyl oxylethyl-2-palmityl imidazoline, 1-stearyl oxyethyl myristyl imidazoline, 1-palmityl oxyethyl-2-palmityl imidazoline, 1-palmityl oxyethyl-2-myristyl imidazoline, 1-stearyl oxyethyl-2-tallow imidazoline, 1-myristyl oxyethyl-2-tallow imidazoline, 1-palmityl oxyethyl-2-tallow imidazoline, 1-coconut oxyethyl-2-coconut imidazoline, 1-tallow oxyethyl-2-tallow imidazoline and mixtures thereof. Also useful is stearyl hydroxyethyl imidazoline, available commercially as ALKAZINE (Alkaril), 1-tallow amido ethyl-2-tallow imidazoline and Methyl-1-tallow amidoethyl-2-tallow imidazoline.

Yet another class of suitable fabric softening materials are the condensation products formed from the reaction of fatty acids with a polyamine selected from the group consisting of hydroxyalkyl, alkylene diamines and dialkylenetriamines and mixtures thereof. Suitable materials are disclosed in EP-A-199382 (Procter). Preferred among these are mixtures of molecules of the generic formula X and corresponding salts obtained by partial protonation.

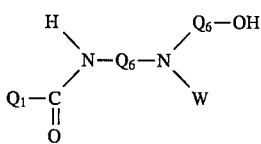

W is selected from hydrogen and the group —C(O)—$Q_1$ and other symbols are as previously defined. Commercially available materials of this class can be obtained from Sandoz Products as Ceranine HC39, HCA and HCPA.

9. Zwitterionic Fabric Softeners

Other useful ingredients of softening systems include zwitterionic quaternary ammonium compounds such as those disclosed in EP 332270 A2 (Unilever) incorporated herein by reference. Representative materials in this class are illustrated by general formula (XI) and (XII)

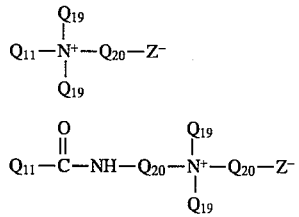

Wherein the groups $Q_{19}$ are selected independently from $Q_7$, $Q_{11}$ and $Q_{14}$; $Q_{20}$ is a divalent alkylene group containing 1 to 3 carbon atoms and may be interrupted by —O—, —CONH, — C(O)O—, etc; and $Z^-$ is an anionic water solubilising group (e.g. carboxy, sulphate, sulpho or phosphonium).

Examples of commercially available materials are the EMPIGEN CD and BS series (Albright Wilson) the REWO-TERIC AM series (Rewo) and the Tegobetain F, H, L and N series (GOLDSCHMIDT).

10. Nonionic Ingredients

It is well known to blend nonionic materials with cationic, amphoteric or zwitterionic softening materials as a means of improving dispersion of the product in rinse waters and enhancing the fabric softening properties of the softener blend.

Suitable nonionic adjuncts include lanolin and lanolin derivatives, fatty acids containing from 10 to 18 carbon atoms, esters of fatty acids containing from 8 to 24 carbon atoms with monohydric alcohols containing from 1 to 3 carbon atoms, and polyhydric alcohols containing 2 to 8 carbon atoms such as sucrose, sorbitan, together with alkoxylated fatty acids, alcohols and lanolins containing an average of not more than 7 alkylene oxide groups per molecule. Suitable materials have been disclosed in EP-A-88520 (Unilever,), EP-A-122141 (Unilever), GB 2157728A (Unilever), GB 8410321 (Unilever) , EP-A-159918 (Unilever), EP-A-159922 (Unilever) and EP-A-79746 (Procter).

Fabric softening compositions generally do not contain anionic detergent active nor bleach, nor detergency builder. It is desirable that the amounts (if any) of anionic detergent active, bleach and detergency builder are all less than the amount of the fabric softening agent.

A fabric softening composition which is intended to be added to rinse water may be in the form of a solid, a powder or tablet for instance, which disperses in the rinse water.

More commonly, a fabric softening composition for addition to rinse water is in the form of a liquid, and is an aqueous dispersion in water. Such a fabric softening composition may contain from 1% to 40% by weight of a fabric softening agent but may contain higher levels from 40% up to 80% or even 90% by weight in a very concentrated product. The composition will usually also contain water, which may provide the balance of the composition.

Liquid fabric softening compositions can be prepared by simply mixing the ingredients, including water, with agitation to disperse the water-insoluble ingredients.

Solid fabric conditioning articles which release a fabric softening agent in a tumble dryer can be designed for single usage or multiple usage.

One such article comprises a sponge material releasably enclosing a composition containing fabric softening agent and perfume so as to impart fabric softness and deodorancy during several drying cycles. This multi-use article can be made by filling a hollow sponge with the composition. In use, the composition melts and leaches out through the pores of the sponge to soften fabrics. Such a filled sponge can be used to treat several loads of fabrics in conventional dryers, and has the advantage that it can remain in the dryer after use and is not likely to be misplaced or lost.

Another article comprises a cloth or paper bag releasably enclosing such a composition and sealed with a hardened plug of the mixture. The action and heat of the dryer opens the bag and releases the composition to perform its softening and delivery of deodorant perfume function.

A highly preferred article comprises a composition containing the softening agent and deodorant perfume releasably impregnating a sheet of woven or non-woven cloth substrate. When such an article is placed in a tumble dryer the heat and tumbling action removes the fabric softening composition from the substrate and transfers it to the fabrics.

A solid product for use in a tumble dryer will generally contain fabric softening agent in an amount from 40% to 95% by weight of the product.

The amount of perfume incorporated in a fabric softening product will lie in the range from 0.01% to 10% by weight.

For fabric conditioning liquids containing less than 40% by weight of fabric softening agent, the amount of perfume is preferably 0.1% to 3% by weight, more preferably 0.1% to 1%, especially 0.1% to 0.3%.

The amount of perfume in very concentrated fabric conditioning liquids may lie in the broader range up to 10% by weight, preferably 2% to 8% by weight, more preferably 3% to 6% by weight.

The amount of perfume in products for use in a tumble dryer is preferably from 2% to 4% by weight of the product.

The deodorant effectiveness of a fabric softening composition which incorporates a perfume composition in accordance with this invention can be assessed by testing in accordance with a Malodour Reduction Value test derived from the test devised by Whitehouse and Carter as published in "The proceedings of the Scientific Section of the Toilet Goods Association", No 48, December 1967 at pages 31–37 under the title "Evaluation of Deodorant Toilet Bars".

The procedure is as follows:

Malodour Reduction Value test comprises the steps of:

(i) selecting pieces of cotton shirt fabric having an area of 20 cm+20 cm or more;

(ii) washing the selected pieces of fabric in a front-loaded drum-type washing machine with an unperfumed washing powder: the composition of this powder is not critical but may be as follows:

|  | Parts by weight |
|---|---|
| Sodium dodecylbenzene sulphonate | 9 |
| C13–15 alcohol 7EO | 4 |
| Sodium tripolyphosphate | 33 |
| Alkaline sodium silicate | 6 |
| Sodium carboxymethyl cellulose | 1 |
| magnesium silicate | 1 |
| Ethylenediamine tetraacetic acid | 0.2 |
| Sodium sulphate | 25 |
| Water | 10.8 |

A suitable concentration in the wash liquor is 10.5 g/liter, (iii) rinsing some of the washed pieces of fabric with water alone, and drying them to provide controls;

(iv) further pieces of fabric are rinsed using water to which is added a fabric softening composition consisting of:

6.25% di(hardened tallow)dimethyl ammonium chloride 0.05% preservative 0.4 % perfume under test balance to 100% water This composition is added to the rinse water in a ratio of 90 ml of fabric softening composition to 24 liters of rinse water, i.e. 3.75 ml per liter of rinse water. Thereafter the fabric pieces are dried;

(v) stitching test and control pieces of fabric into clean polyester cotton shirts in the underarm region in accordance with a statistical design;

(vi) causing the shirts carrying the inserts to be worn by a panel of 40 Caucasian male subjects of age within a range from 20 to 55 years (the subjects being chosen from those who develop auxiliary body malodour that is not unusually strong and who do not develop a stronger body malodour in one axilla compared with the other);

(vii) assessing the body malodour of the fabric inserts after a period of five hours whereby three trained female assessors scored the olfactory intensity of malodour on a 0 to 5 scale, 0 representing no odor and 5 representing very strong malodour, the strength of the odor in each instance being related for purposes of comparison to standard odors produced by aqueous solutions of isovaleric acid at different concentrations according to the following table:

| Score | Odour Level | Conc. of aqueous isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very Strong | 3.57 |

(viii) calculating the average scores for test fabric pieces and control fabric pieces, and subtracting the average score for test pieces from the average score of the control pieces to arrive at the Malodour Reduction Value for the perfume composition under test.

A number of perfume compositions illustrating the invention are set out in the following non-limitative examples.

Where a material falls within one of the categories set forth above, this is indicated by the words "ketone", "alcohol", "acetate", "propionate", "salicylate" or ether. Materials in the category of aldehydes of formula $R^7CHO$ and galaxolide are indicated by the abbreviation "aldh/glax".

Some materials denoted by trade marks or trivial names have been identified more fully above. Perfume bases denoted by the letters AB and a number are mixtures of materials marketed by Quest International, Naarden, Netherlands. They may contain additional quantities of materials within the categories defined above.

EXAMPLE 1

A low odor perfume composition is as follows:

| % by weight | Ingredient | Category |
|---|---|---|
| 8.0 | Benzyl Alcohol |  |
| 7.5 | Benzyl Salicylate | salicylate |
| 2.0 | Cedar wood oil (Virginian) |  |
| 10.0 | Galaxolide | aldehyde |
| 10.0 | Diethyl Phthalate |  |
| 1.0 | Grisalva (10% solution in dipropylene glycol) (IFF) |  |
| 5.0 | Hercolyn D (Hercules) |  |
| 3.0 | Isobutyl Benzoate |  |
| 2.0 | Isobutyl Cinnamate |  |
| 1.0 | Linalyl Cinnamate |  |
| 5.0 | Moss Base AB 7004 (*) |  |
| 20.0 | Muguet Base AB 7001 (*) |  |
| 5.0 | Tonalid | ketone |
| 20.0 | Traseolide (*) | ketone |

(*) = available from Quest International

The odor type of this formulation is mildly woody, mossy, moguet and musk.

This perfume composition was tested for deodorant action in a fabric softening composition using the test described above. The results are quoted after Example 7 below.

EXAMPLE 2

A further and highly preferred composition for extremely low odor intensity is as follows:

| % by weight | Ingredient | Category |
|---|---|---|
| 5.0 | Benzyl Alcohol | |
| 4.0 | Benzyl Cinnamate | |
| 20.0 | Benzyl Salicylate | salicylate |
| 1.0 | Cinnamyl Cinnamate | |
| 9.0 | Diethyl Phthalate | |
| 4.0 | Galaxolide | aldh/glax |
| 20.0 | Jasmin AB 7002 (*) | |
| 5.0 | Linalyl Cinnamate | |
| 2.0 | Sandalone AC 802 (*) | |
| 30.0 | Traseolide (*) | ketone |
| 100.0 | | |

(*) = available from Quest International

The odor type of this formulation is mildly sweet, floral and musk.

EXAMPLE 3

A further example of a low odor perfume composition is as follows:

| % by weight | Ingredient | Category |
|---|---|---|
| 18.0 | Benzyl Salicylate | salicylate |
| 7.0 | Diethyl Phthalate | |
| 5.0 | Ethylene Brassylate | |
| 5.0 | Galaxolide | aldh/glax |
| 20.0 | Muguet AB 7001 (*) | |
| 2.0 | Phenylethyl Salicylate | salicylate |
| 2.0 | Sandalone AC 802 (*) | |
| 3.0 | Sandela (Givauden) | |
| 38.0 | Traseolide (*) | ketone |
| 100.0 | | |

(*) = available from Quest International

The odor type of this formulation is mildly moguet and musk.

EXAMPLE 4

A further example of a low odor perfume composition is as follows:

| % by weight | Ingredient | Category |
|---|---|---|
| 5.0 | Benzyl Alcohol | |
| 8.0 | Benzyl Benzoate | |
| 5.0 | Benzyl Cinnamate | |
| 5.0 | Carnation AB 7005 (*) | |
| 2.0 | Copaiba Balsam | |
| 5.0 | Galaxolide | aldh/glax |
| 15.0 | Hexyl Salicylate | salicylate |
| 15.0 | Jasmin Base AB 7002 (*) | |
| 35.0 | Traseolide (*) | ketone |
| 5.0 | Diethyl Phthalate | |
| 100.0 | | |

(*) = availabel from Quest International

The odor type of this formulation is mildly spicy, jasmine and musk.

Odor Intensity Indices

The odor intensities of the above four examples were assessed by a panel and found to be not more intense than a 5% solution of benzyl acetate in dipropylene glycol, and significantly less intense than a 10% solution.

EXAMPLES 5 to 7

Further perfume compositions of more perceptible fragrance but also in accordance with this invention, were made and tested for deodorant action in a fabric softening composition, using the test for Malodour Reduction Value described above.

These examples use a number of materials which are denoted by trade marks or trivial names, other than those already identified above. These are:

| | |
|---|---|
| raspberry ketone | 4-(parahydroxyphenyl)butan-2-one |
| dimyrcetol | A mixture of materials marketed under this name by International Flavours and Fragrances. The mixture includes approximately equal amounts of the alcohol dihydromyrcenol and its formate ester. |
| aurantion | methyl N-(3,7-dimethyl-7-hydroxy-octylidene) anthranilate |
| precious wood } base AB 401 } | Mixture of materials marketed by Quest International, Naarden, Netherlands |
| rosenta AB 380 } | Mixture of materials marketed by Quest International, Naarden, Netherlands |
| rose acetone | alpha-trichloromethylbenzyl acetate |
| lyral | 4-(4'-methyl-4'-hydroxypentyl)-3-cyclohexene carboxaldehyde |
| alpha-isomethyl ionone | 1-methyl-2(2',6',6'-trimethyl cyclohex-2-enyl)vinyl methyl ketone |
| iso-E super | 1,2,3,5,6,7,8-octahydro-2,3,8,8-tetramethyl-2-acetyl napthalene |
| hedione | also known as methyl dihydrojasmonate, is 2-amyl-3-methoxycarbonyl-methylcyclopentanone |

EXAMPLE 5

| Ingredient | Category | % by weight |
|---|---|---|
| Tonalid | ketone | 3 |
| traseolide | ketone | 5 |
| dimyrcetol | alcohol (50%) | 2.5 |
| tetrahydrolinalol | alcohol | 6 |
| 9-decen-1-ol | alcohol | 0.5 |
| florocyclene | acetate | 2.2 |
| para tert butyl cyclohexyl acetate | acetate | 7 |
| dimethylbenzylcarbinyl-acetate | acetate | 2.5 |
| ortho tert butyl cyclohexyl acetate | acetate | 1.4 |
| benzyl salicylate | salicyl. | 6 |
| yara | ether | 0.1 |
| galaxolide | aldh/glax | 5 |
| hexyl cinnamic aldehyde | aldh/glax | 11 |
| lilial | aldh/glax | 10 |
| coumarin | | 2 |
| precious wood base AB 401 | | 3.8 |
| rose acetone | | 1 |
| acetyl cedrene | | 3.7 |
| benzyl acetate | | 3.5 |
| aurantion | | 2 |
| eugenol | | 0.5 |
| patchouli oil | | 1.8 |
| phenyl ethyl alcohol | | 7 |
| diethylphthalate | | 5 |
| alpha iso methyl ionone | | 5 |

| Ingredient | Category | % by weight |
|---|---|---|
| hedione | | 2.5 |
| | | 100 |

EXAMPLE 6

| Ingredient | Category | % by weight |
|---|---|---|
| tonalid | ketone | 11 |
| traseolide | ketone | 5.5 |
| tetrahydrolinalol | alcohol | 6 |
| dihydromyrcenol | alcohol | 2 |
| florocyclene | acetate | 3 |
| para tert butyl cyclohexyl acetate | acetate | 6.6 |
| dimethylbenzylcarbinyl-acetate | acetate | 1 |
| ortho tert butyl cyclohexyl acetate | acetate | 1.5 |
| hexyl salicylate | salicyl. | 4.5 |
| benzyl salicylate | salicyl. | 2 |
| hexyl cinnamic aldehyde | aldh/glax | 16 |
| lilial | aldh/glax | 10 |
| aurantion | | 2.2 |
| linalol | | 2 |
| acetyl cedrene | | 4.5 |
| undecalactone gamma | | 0.2 |
| methyl cinnamate | | 0.7 |
| benzyl acetate | | 2.8 |
| lyral | | 0.2 |
| phenyl ethyl alcohol | | 6 |
| raspberry ketone | | 1 |
| alpha iso methyl ionone | | 3 |
| rosenta AB 380 | | 4.5 |
| iso-E super | | 1.8 |
| hedione | | 2 |
| | | 100 |

EXAMPLE 7

| Ingredient | Category | % by weight |
|---|---|---|
| tonalid | ketone | 15 |
| traseolide | ketone | 6 |
| tetrahydrolinalol | alcohol | 5.5 |
| dihydromyrcenol | alcohol | 2 |
| florocyclene | acetate | 3 |
| para tert butyl cyclohexyl acetate | acetate | 5 |
| dimethylbenzylcarbinyl-aCetate | acetate | 1 |
| ortho tert butyl cyclohexyl acetate | acetate | 1.6 |
| hexyl salicylate | salicyl. | 6.5 |
| benzyl salicylate | salicyl. | 2 |
| yara | ether | 0.5 |
| hexyl cinnamic aldehyde | aldh/glax | 15 |
| lilial | aldh/glax | 10 |
| coumarin | | 1.8 |
| aurantion | | 2 |
| acetyl cedrene | | 3.8 |
| methyl cinnamate | | 0.8 |
| benzyl acetate | | 2.5 |
| phenyl ethyl alcohol | | 7.5 |
| raspberry ketone | | 1 |
| rosenta AB 380 | | 5.5 |
| iso-E super | | 2 |

| Ingredient | Category | % by weight |
|---|---|---|
| | | 100 |

The results obtained in the Malodour Reduction Value test are set out in the following table.

| | Control | Average panel score | Malodour Reduction Value |
|---|---|---|---|
| Example 1 | 3.50 | 2.01 | 1.49 |
| Example 5 | 2.99 | 1.54 | 1.45 |
| Example 6 | 3.50 | 2.17 | 1.33 |
| Example 7 | 3.50 | 2.11 | 1.39 |

Comparison of Odor Character

Perfumes according to Examples 5 to 7 above and one of the perfume compositions exemplified in US-A-4134838 were assessed for the character of their fragrances.

This assessment was carried out by a panel of thirty persons trained to recognize and discriminate between fragrance characteristics, e.g. floral, spicy etc. Each panelist was required to estimate the intensity of various characteristics in each perfume, relative to a standard material having the characteristic concerned. The panelists' scores were placed on a uniform scale and then averaged for each characteristic for each individual perfume. The scale was arranged to run from zero (denoting absence of the characteristic) to 2 (denoting the strongest individual characteristic which was "sharp" in the composition from US-A-4134838. On this scale the intensities of the individual characteristics in the standard materials were approximately 5.

The fragrance characteristics assessed included some which, although not necessarily unpleasant in themselves, are powerful and distinctive odors. Consequently, if these are perceptible in too great a degree in a perfume composition, they can render that perfume composition excessively distinctive and/or unattractive to a consumer or unsuitable for its intended application. Accordingly these characteristics should not dominate in a well balanced perfume.

The various fragrance characteristics which were assessed also included some which are generally considered attractive for the perfume of a fabric softening product.

The panel scores for individual characteristics in each perfume are set out in the following table.

The characteristic called "Mixed Florals" in the table is an overall score for eight individual characteristics which are the odors of individual flower species (carnation, hyacinth, jasmine, lilac, lily of the valley, narcissus, rose and violet).

| Perfume Characteristic | Invention | | | US 4134838 |
|---|---|---|---|---|
| | Ex 5 | Ex 6 | Ex 7 | Composition C1 |
| Sharp | 0.64 | 0.64 | 0.51 | 2.00 |
| Spicy | 0.26 | 0.13 | 0.26 | 0.64 |
| Citrus | 0.64 | 0.77 | 0.90 | 1.92 |
| Herbal | 0.13 | 0.13 | 0.26 | 0.38 |
| Heavy floral | 0.64 | 0.77 | 0.64 | 0.90 |
| Chemical | 0.13 | 0.13 | 0.00 | 0.38 |
| Woody | 0.64 | 0.38 | 0.26 | 0.90 |

-continued

| Perfume Characteristic | Invention | | | US 4134838 |
| --- | --- | --- | --- | --- |
| | Ex 5 | Ex 6 | Ex 7 | Composition C1 |
| Green | 0.13 | 0.00 | 0.00 | 0.26 |
| Light floral | 0.64 | 0.64 | 0.51 | 0.51 |
| Disinfectant | 0.38 | 0.26 | 0.13 | 0.90 |
| Floral | 0.77 | 0.90 | 0.90 | 0.90 |
| Mixed florals | 1.15 | 1.15 | 1.28 | 0.64 |
| Powdery | 1.41 | 1.79 | 1.66 | 0.51 |
| Fragrant | 1.41 | 1.15 | 1.41 | 1.66 |

We claim:

1. A fabric conditioning product comprising
   (i) from 1% to 95% by weight of a fabric softening agent and
   (ii) from 0.01% to 10% by weight of a perfume composition in which at least 30% by weight of the perfume composition is constituted by materials from the following categories:
   at least 7% by weight of the perfume composition of one or more aromatic methyl ketones of general formula $$R^3-\overset{O}{\underset{\|}{C}}-CH_3$$

in which $R^3$ is an aromatic group such that the molecular weight of the ketone is from 170 to 300; and
   at least 3% by weight of the perfume composition of one or more salicylates of general formula

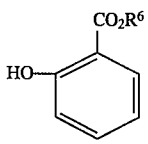

in which $R^6$ is an aliphatic group, optionally containing not more than one olefinic double bond, and optionally bearing an aromatic substituent group, such that the molecular weight of the salicylate is in the range 190 to 230.

2. A fabric conditioning composition according to claim 1 in which the perfume composition further comprises
   at least 5% by weight of the perfume composition of one or more ingredients selected from the group consisting of alcohols of general formula $$R^4OH$$

acetates of general formula $$CH_3CO_2R^5$$

propionates of general formula $$C_2H_5CO_2R^5$$

in which $R^4$ is an aliphatic group, optionally containing not more than one olefinic double bond, and optionally bearing an aromatic substituent group, such that the molecular weight of the alcohol is in the range 130 to 180; and
   $R^5$ is an aliphatic group optionally containing not more than one olefinic double bond, and optionally bearing an aromatic substituent group such that the molecular weight of the acetate or propionate is in the range 180 to 210.

3. A fabric conditioning product according to claim 2 in which the perfume composition further comprises at least 4% by weight of the perfume composition of said alcohols and also comprise at least 5% by weight of the perfume composition of one or more said acetates or propionates.

4. A fabric conditioning product according to claim 2 in which the perfume composition further comprises at least 0.05% by weight of the perfume composition of one or more ethers of formula $$R^1OR^2$$

wherein $R^1$ and $R^2$ are connected through the ether oxygen atom and $R^1$ and $R^2$ each represent an aliphatic or an aromatic group such that the ether has a molecular weight of 150 to 200.

5. A fabric conditioning product according to claim 1 in which the perfume composition comprises at least 2% by weight of the perfume composition of one or more aldehydes of formula $R^7CHO$ in which $R^7$ is an aliphatic group, optionally containing not more than one olefinic double bond, and optionally bearing an aromatic substituent group, such that the molecular weight of the aldehyde is in the range 180 to 220.

6. A fabric conditioning product according to claim 1, in which the perfume composition comprises at least 2% by weight of the perfume composition of 1,3,4,6,7,8-hexahydro-4,6,6,7,8,8-hexamethyl cyclopenta-2-benzopyran.

7. A fabric conditioning product according to claim 2, in which the perfume composition comprises at least 2% by weight of the perfume composition of 1,3,4,6,7,8-hexahydro-4,6,6,7,8,8-hexamethyl cyclopenta-2-benzopyran.

8. A fabric conditioning product according to claim 2 wherein the perfume composition contains
   at least 4% of said alcohols, which do not include any alcohol which is also an ester, and
   at least 7% of said ketones, which do not include any ketone which is also an ester or an alcohol.

9. A fabric conditioning product according to claim 8 wherein the specified quantities of said ketones, alcohols, acetates or propionates, and salicylates are provided by materials which are not aldehydes.

10. A fabric conditioning product according to claim 2 wherein the perfume composition comprises
    from 7% to 50% by weight of the perfume composition of one or more said ketones, not including any ketone which is also an alcohol,
    from 4% to 50% by weight of the perfume composition of one or more said alcohols, not including any alcohol which is also an ester,
    from 4% to 40% by weight of the perfume composition of an ester selected from the group consisting of said acetates and propionates,
    from 3% to 60% by weight of the perfume composition of one or more said salicylates, and
    from 0.1% to 20% by weight of the perfume composition of one or more ethers of formula $$R^1OR^2$$

wherein $R^1$ and $R^2$ are connected through the ether oxygen atom and $R^1$ and $R^2$ each represent an aliphatic or an aromatic group such that the ether has a molecular weight of 150 to 200.

11. A fabric conditioning product according to claim 10 wherein the fabric softening agent comprises an organic quaternary nitrogen compound having at least one carbon chain of 6 to 30 carbon atoms.

12. A method of perfuming fabrics comprising laundering the fabrics and then rinsing the fabrics in an aqueous rinse liquor containing a composition as defined in claim 1.

* * * * *